United States Patent
Kennedy

[19]

[11] Patent Number: 5,999,856
[45] Date of Patent: Dec. 7, 1999

[54] IMPLANTABLE HEARING ASSISTANCE SYSTEM WITH CALIBRATION AND AUDITORY RESPONSE TESTING

[75] Inventor: Joel A. Kennedy, Arden Hills, Minn.

[73] Assignee: St. Croix Medical, Inc., Minneapolis, Minn.

[21] Appl. No.: 08/804,016

[22] Filed: Feb. 21, 1997

[51] Int. Cl.$^6$ ..................................................... A61N 1/18
[52] U.S. Cl. .................. 607/57; 600/559; 381/60
[58] Field of Search .............................. 607/55–57, 136, 607/137; 73/585; 600/559, 25; 381/312, 23.1, 60; 623/10

[56] References Cited

U.S. PATENT DOCUMENTS

| | | | |
|---|---|---|---|
| 4,615,007 | 9/1986 | King et al. .............................. | 600/559 |
| 4,953,112 | 8/1990 | Widin et al. ........................... | 600/559 |
| 5,105,822 | 4/1992 | Stevens et al. ........................ | 600/559 |
| 5,282,475 | 2/1994 | Urbach et al. ......................... | 600/559 |
| 5,282,858 | 2/1994 | Bisch et al. . . | |
| 5,522,386 | 6/1996 | Lerner .................................... | 600/559 |
| 5,651,371 | 7/1997 | Keefe .................................... | 600/559 |
| 5,682,882 | 11/1997 | Lieberman ............................. | 600/559 |

Primary Examiner—Kennedy J. Schaetzle
Attorney, Agent, or Firm—Patterson & Keough, P.A.

[57] ABSTRACT

A hearing assistance system includes electric response audiometry (ERA) functions for diagnostic, self-calibration, frequency-response parameter adjustment, feedback self-testing, and automatic gain control (AGC) purposes. The invention includes partial middle ear implantable (P-MEI), total middle ear implantable (T-MEI), cochlear implant, or other hearing assistance systems. Auditory response signals are obtained by auditory brain-stem response (ABR), cortical ERA, and electrocochleography. A mechanical vibration or electrical stimulus is introduced directly in the middle or inner ear, either in response to an input signal corresponding to sound, or in response to an independent calibration signal. Auditory response signals are obtained by surface electroencephalography (EEG) or by an implanted electrocochleographic sensor. Calibration stimuli have constant or adjustable amplitudes, frequencies, and repetition frequencies. Wide-band clicks, pure audio tones, and other calibration stimuli are included. The diagnostic and calibration capabilities are particularly useful to assess efficacy during implantation of components into a patient under general anesthesia.

15 Claims, 9 Drawing Sheets

IMPLANTABLE HEARING ASSISTANCE SYSTEM WITH CALIBRATION AND AUDITORY RESPONSE TESTING

THE FIELD OF THE INVENTION

This invention relates generally to an at least partially implantable hearing assistance system, and more particularly to the calibration or adjustment of such a hearing assistance system, and also to testing a patient's auditory response.

BACKGROUND

Some types of partial middle ear implantable (P-MEI), total middle ear implantable (T-MEI), cochlear implant, or other hearing assistance systems utilize components disposed within the middle ear or inner ear regions. Such components might include an input transducer for receiving sound vibrations or an output stimulator for providing mechanical or electrical output stimuli corresponding to the received sound vibrations.

An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus, transducing mechanical energy into an electrical signal, which is amplified and further processed by an electronics unit. A resulting electrical signal is provided to an electrical-to-mechanical piezoelectric output transducer that generates a mechanical vibration coupled to an element of the ossicular chain or to the oval window or round window for assisting hearing. In the '366 patent, the ossicular chain is interrupted by removal of the incus. Removal of the incus prevents the mechanical vibrations delivered by the piezoelectric output transducer from mechanically feeding back to the piezoelectric input transducer.

Introducing components into the middle or inner ear regions typically involves intricate surgical procedures for positioning or affixing the components for communication or coupling to the desired auditory elements. The proper positioning and affixation for obtaining the best input signal and providing the best output stimuli is a difficult task. The patient is typically under general anesthesia, and is thus unable to provide the implanting physician with any information regarding how well sound is being perceived. Thus, the implanting surgeon faces a difficult task that may yield uneven results in the proper positioning and affixation of components in the middle or inner ear regions in order to obtain proper sound perception.

Other complicating factors are also present. There may be a large variations between patients in the sound perception characteristics of their auditory systems. Moreover, there may be variations between hearing assistance systems, such as in their component characteristics, for example, the characteristics of the input transducer and output stimulator may well vary to some degree. There is a need in the art for hearing assistance systems to provide diagnostic or calibration information to the physician, such as during the surgical implantation procedure, in order to ascertain efficacy and adjust therapy accordingly. There is a further need in the art for self-calibration of such hearing assistance systems to increase their ease of use.

SUMMARY

The present invention provides a method of testing an auditory response in a living organism. A stimulus is introduced directly into the middle or inner ear. An electrical auditory response signal is obtained in response to the stimulus.

Another such method includes applying sound to an ear. The sound is transduced into an electrical input signal. The electrical input signal is processed to provide a resulting electrical output signal. An output stimulus is introduced directly in the middle ear or inner ear in response to the electrical output signal. An electrical auditory response signal is obtained in response to the output stimulus.

In one embodiment, the invention provides a method of assisting hearing using an at least partially implantable hearing assistance device. An output stimulator is positioned in a middle or inner ear for providing a stimulus thereto. An auditory response to the stimulus is measured. The output stimulator is repositioned if the measured auditory response does not exceed a threshold value.

In another calibration method, an output stimulator is positioned in a middle or inner ear for providing a calibration stimulus thereto. An auditory response to the calibration stimulus is measured. Characteristics of an electrical signal, provided to the output stimulator in response to transduced sounds, are adjusted.

In another calibration method, an input transducer is positioned in the middle ear. An output stimulator is positioned in the middle or inner ear. Sound is provided to and received by the input transducer. An output stimulus is provided by the output stimulator in response to the sound received by the input transducer. An auditory response signal to the output stimulus is measured. At least one signal processing parameter is adjusted based upon the measured auditory response signal.

In another method of using an at least partially implantable hearing assistance device, such as for calibration, a calibration stimulus is provided to the middle or inner ear via an output stimulator. A feedback signal is detected, such as at an input transducer. A characteristic of the calibration stimulus is changed, based upon the detected feedback signal. In one embodiment, for example, the amplitude of the calibration stimulus is increased if the detected feedback signal does not meet a threshold value. In another embodiment, a signal processing parameter is adjusted if the detected feedback signal does meet the threshold. In a further embodiment, the above-described calibration is repeated over a range of frequencies to obtain a calibrated frequency response.

The system also provides an apparatus, which may be used for assisting hearing or testing an auditory response. An input transducer converts a sound wave or mechanical vibration into an electrical input signal. An output stimulator is proportioned for disposition within a middle or inner ear region of an ear. The output stimulator receives an output electrical signal from an implantable electronics unit in response to the input electrical signal. In one embodiment, the electronics unit includes a calibration module that provides an output calibration signal to the output stimulator.

In another embodiment, the system comprises an input transducer for converting a sound wave or mechanical vibration into an electrical input signal. An output stimulator is proportioned for disposition within the middle ear region or an inner ear region of an ear. The output stimulator receives an output electrical signal from an implantable electronics unit in response to the input electrical signal. A response sensor is also included for providing an auditory response signal. In one embodiment, the response sensor includes an external EEG device and a surface electrode. In another embodiment, the response sensor includes an implantable electrode for providing the auditory response signal to the electronics unit.

Thus, the present invention provides a hearing assistance system for testing an auditory response. The system provides diagnostic or calibration information to the physician, which is particularly useful during implantation of middle or inner ear components; a patient under general anesthesia is unable to independently provide the physician with any information regarding the adequacy of sound perception. The invention also provides for feedback detection and self-calibration to increase its ease of use.

BRIEF DESCRIPTION OF THE DRAWINGS

In the drawings, like numerals describe substantially similar components throughout the several views.

DETAILED DESCRIPTION

Figure 1:
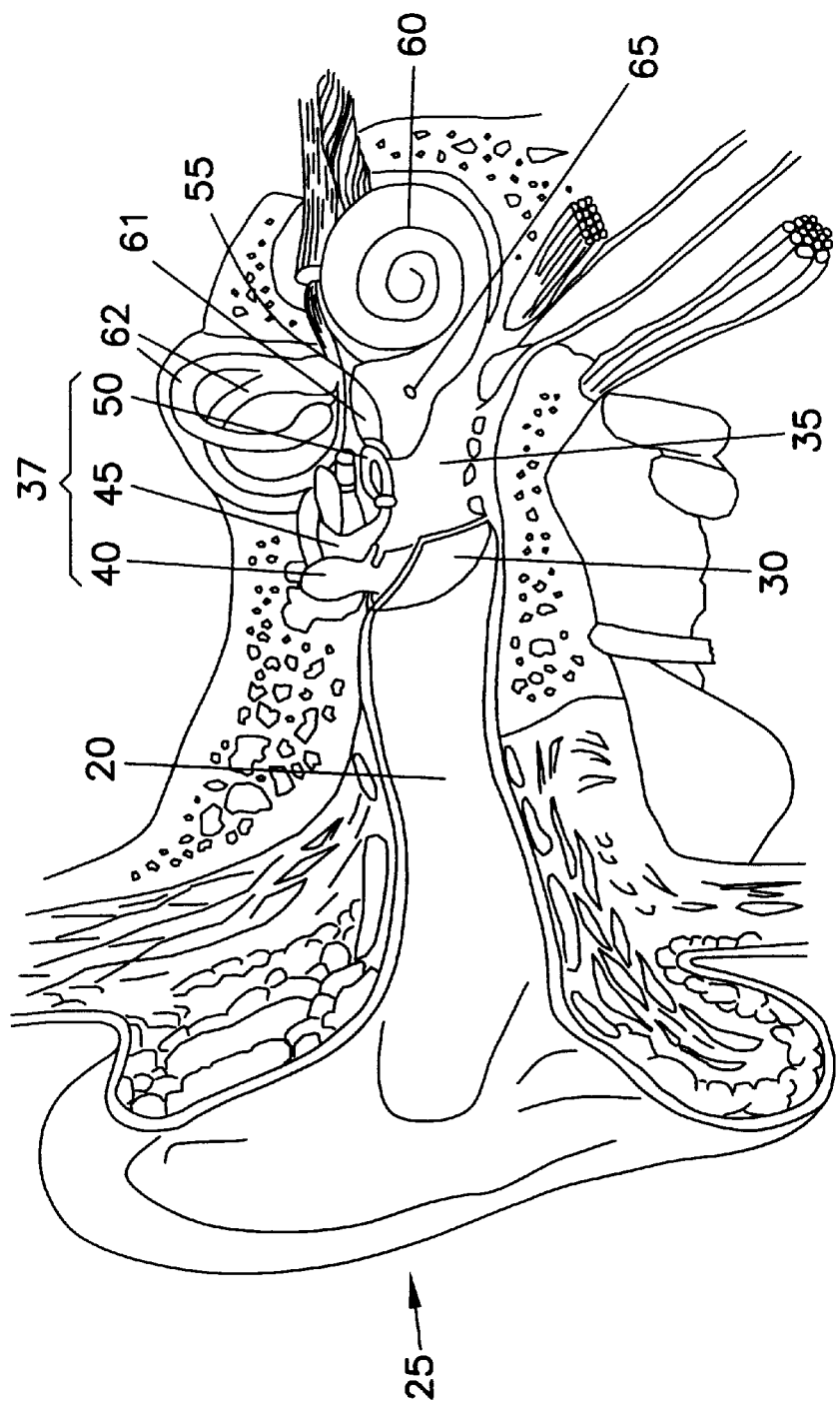
FIG. 1 illustrates a frontal section of an anatomically normal human ear in which the invention operates.

The present invention provides a hearing assistance system having built-in diagnostic and calibration capability. The hearing assistance system is capable of use as or with a middle ear implantable hearing system such as a partial middle ear implantable (P-MEI), total middle ear implantable (T-MEI), cochlear implant, or other hearing system. A P-MEI or T-MEI hearing system assists the human auditory system in converting acoustic energy contained within sound waves into electrochemical signals delivered to the brain and interpreted as sound. FIG. 1 illustrates generally a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as an ossicular chain 37. Thus, the tympanic membrane 30 and ossicular chain 37 transform acoustic energy in the external auditory canal 20 to mechanical energy at the cochlea 60.

The ossicular chain 37 includes three primary components: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The footplate portion of stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea 60 is referred to as sensorineural hearing loss. Hearing loss due to an inability to conduct mechanical vibrations through the middle ear 35 is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in an unwanted feedback signal which degrades sound quality. For example, the unwanted feedback signal may limit the volume, i.e. signal amplitude, of the sound that can be transmitted to the tympanic membrane 30. Conventional hearing aids also often suffer from a significant amount of signal distortion.

Implantable hearing systems have also been developed, utilizing various approaches to compensate for hearing disorders. For example, cochlear implant techniques are used to implement an inner ear hearing system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing systems have been developed to aid patients not having an intact tympanic membrane 30, upon which "air conduction" hearing aids depend. For example, temporal bone conduction hearing systems produce mechanical vibrations that are coupled to the cochlea 60 via a temporal bone in the skull. In such temporal bone conduction hearing systems, a vibrating element can be implemented percutaneously or subcutaneously.

A particularly interesting class of hearing systems includes those which are configured for disposition principally within the middle ear 35 space. In middle ear implantable (MEI) hearing assistance systems, an electrical-to-mechanical output transducer couples mechanical vibrations to the ossicular chain 37, which is optionally interrupted to allow this coupling of the mechanical vibrations to the ossicular chain 37. Both electromagnetic and piezoelectric output transducers have been used to effect the mechanical vibrations upon the ossicular chain 37.

One example of a partial middle ear implantable (P-MEI) hearing system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption requiring larger batteries, which limits their usefulness in total middle ear implantable (T-MEI) hearing systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed by an electronics unit. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

As discussed above, the implanting surgeon faces a difficult task in the proper positioning and affixation of components within the middle ear 35 or inner ear regions in P-MEI, T-MEI, cochlear implant, or other hearing assistance systems in order to obtain proper sound perception. The present invention includes a hearing assistance system having built-in diagnostic and calibration capability that is particularly useful during the surgical implantation procedure, in order to ascertain efficacy and adjust therapy accordingly. As will be described below, the present invention includes self-calibration, frequency response self-calibration, feedback self-test, and automatic gain control (AGC) embodiments of the hearing assistance systems in order to increase its effectiveness and ease of use.

Figure 2:
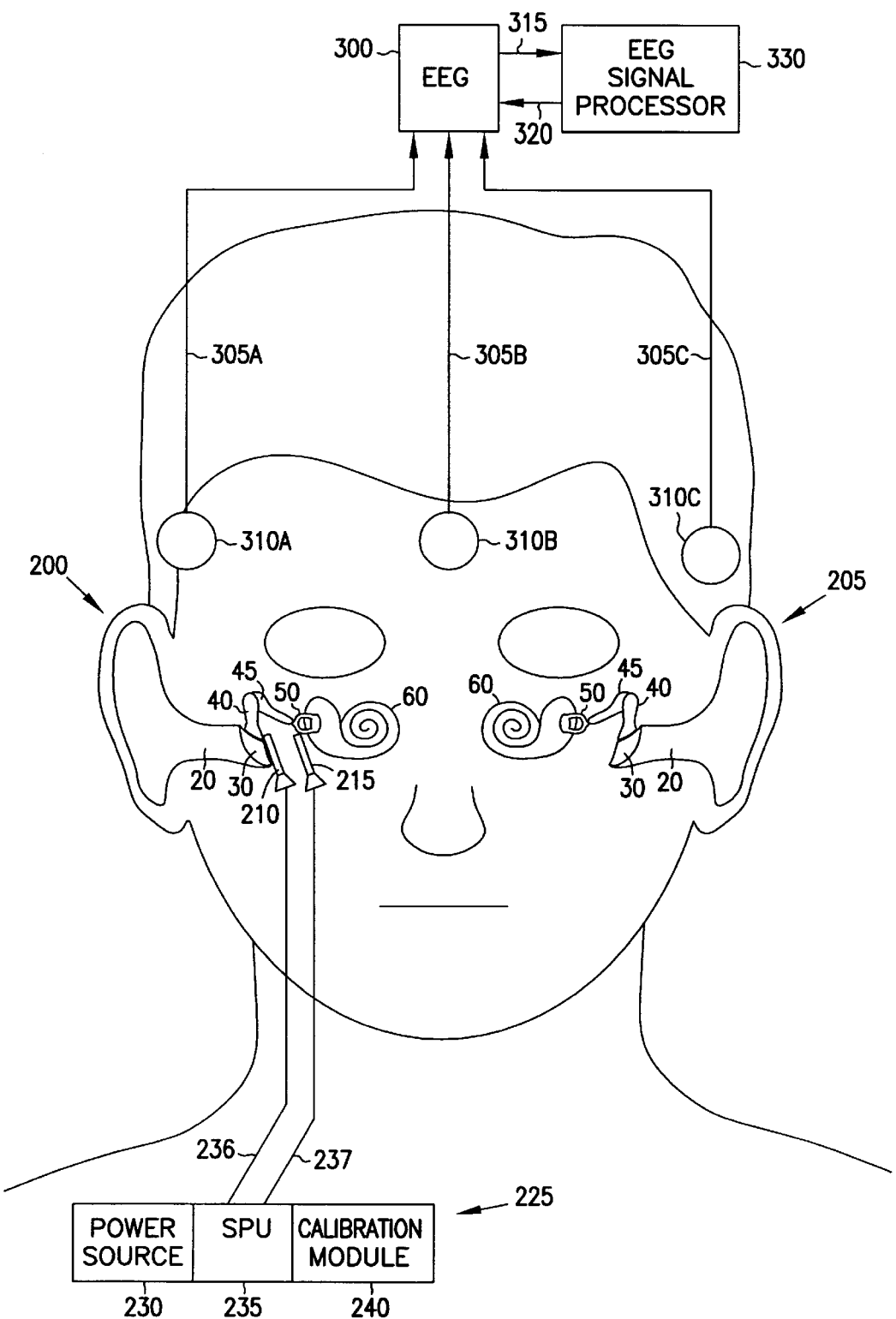
FIG. 2 is a generalized schematic illustration of a frontal view of a person with cutaway views of each ear, including one embodiment of the invention partially disposed in one ear.

FIG. 2 is a generalized schematic illustration of one embodiment of the present invention. FIG. 2 illustrates a frontal view of a person with cutaway views of the anatomical features of each of a right ear 200 and a left ear 205. Input transducer 210 and output stimulator 215 are introduced into the middle ear 35 or inner ear regions of right ear 200 or left ear 205. In one embodiment, input transducer 210 is an electromechanical transducer for receiving mechanical sound vibrations in the middle ear 35 region. In another embodiment, input transducer 210 is a microphone for receiving sound waves in the middle ear 35 region. Input transducer 210 provides a resulting electrical input signal through subcutaneous input lead 236 to electronics unit 225. Electronics unit 225 provides through subcutaneous output lead 237 an electrical output signal to output stimulator 215. In one embodiment, output stimulator 215 is an electromechanical output transducer, for producing mechanical vibrations that are coupled to stapes 50 or other suitable auditory element in order to assist hearing. Such an electromechanical output transducer may include piezoelectric, electromagnetic, or other suitable output transducer elements. In one embodiment, incus 45 is removed from right ear 200 to prevent unwanted mechanical feedback of mechanical vibrations from output stimulator 215 to input transducer 210.

Electronics unit 225 may be locally implanted in the mastoid portion of the patient's temporal bone, or remotely implanted in the patient's pectoral region or elsewhere. Electronics unit 225 includes power source 230, signal processing unit (SPU) 235, and calibration module 240. SPU 235 performs amplification and other signal processing of the input signal received through input lead 236 and provides the resulting output signal through output lead 237 to output stimulator 215. As discussed below, calibration module 240, which may be incorporated into SPU 235 and may also be triggered externally, provides electrical calibration output signals through output lead 237 to output stimulator 215; the calibration output signals are typically independent of, i.e. not in response to, the input signals received through input lead 236. Output stimulator 215 provides an output stimulus, such as a mechanical vibration, in response to the output signal received through output lead 237. Output stimulator 215 also provides a calibration stimulus, such as a mechanical vibration, in response to the calibration output signals received through output lead 237.

In the above-described embodiment, electrical brain waves are received by a response sensor, which includes electroencephalography (EEG) device 300. An auditory response signal, i.e. the portion of the received brain waves resulting from auditory neural pathway's response to the calibration stimuli, is extracted through electric response audiometry (ERA), such as through auditory brain-stem response (ABR), cortical electric response, electrocochleography, or other known audiometric techniques. In this embodiment, EEG device 300 is electrically coupled through external leads 305A–C to external surface electrodes 310A–C. Electrodes 310A–C typically comprise a ground electrode and two signal electrodes that are suitably placed for reception of the brain waves. For example, one of electrodes 310A–C is placed on the scalp vertex or the forehead, and each of the other two of electrodes 310A–C are placed on opposing mastoid prominences or earlobes. EEG device 300 typically includes a differential amplifier for amplification of the received brain waves. EEG device 300 may also include filtering circuits and a display monitor for observation of the brain waves and other electrical signals. In this embodiment, EEG device 300 provides a resulting EEG output signal through EEG output node 315 to EEG signal processor 330.

EEG signal processor 330 includes filtering, averaging, and correlation functions to extract the auditory response signal from the brain waves received at EEG output node 315. EEG signal processor 330 provides the resulting auditory response signal, either on its own display monitor, or through auditory response signal output node 320 for display on any monitor in EEG device 300. EEG signal processor 330 may also provide other diagnostic information, such as an indicator of the maximum amplitude of the auditory response signal. As described below, extraction of the auditory response signal may include both unsynchronized mode and synchronized mode embodiments.

In an unsynchronized mode, the calibration output signal provided by calibration module 240 to output stimulator 215 produces repeated calibration stimuli. Each calibration stimulus is in a known timing relationship to previous and subsequent calibration stimuli. For example, the calibration output signals provided by calibration module 240 typically produce repeated calibration stimuli separated by a known fixed time interval, such as 10 milliseconds, which is longer than a response time of the auditory neural pathway for most patients. In one embodiment, EEG signal processor 330 uses a measuring window, of similar duration as the time interval between calibration stimuli, to perform its averaging and correlation functions. An average auditory response signal is obtained by measuring the auditory response signals to multiple calibration stimuli.

Figure 3:
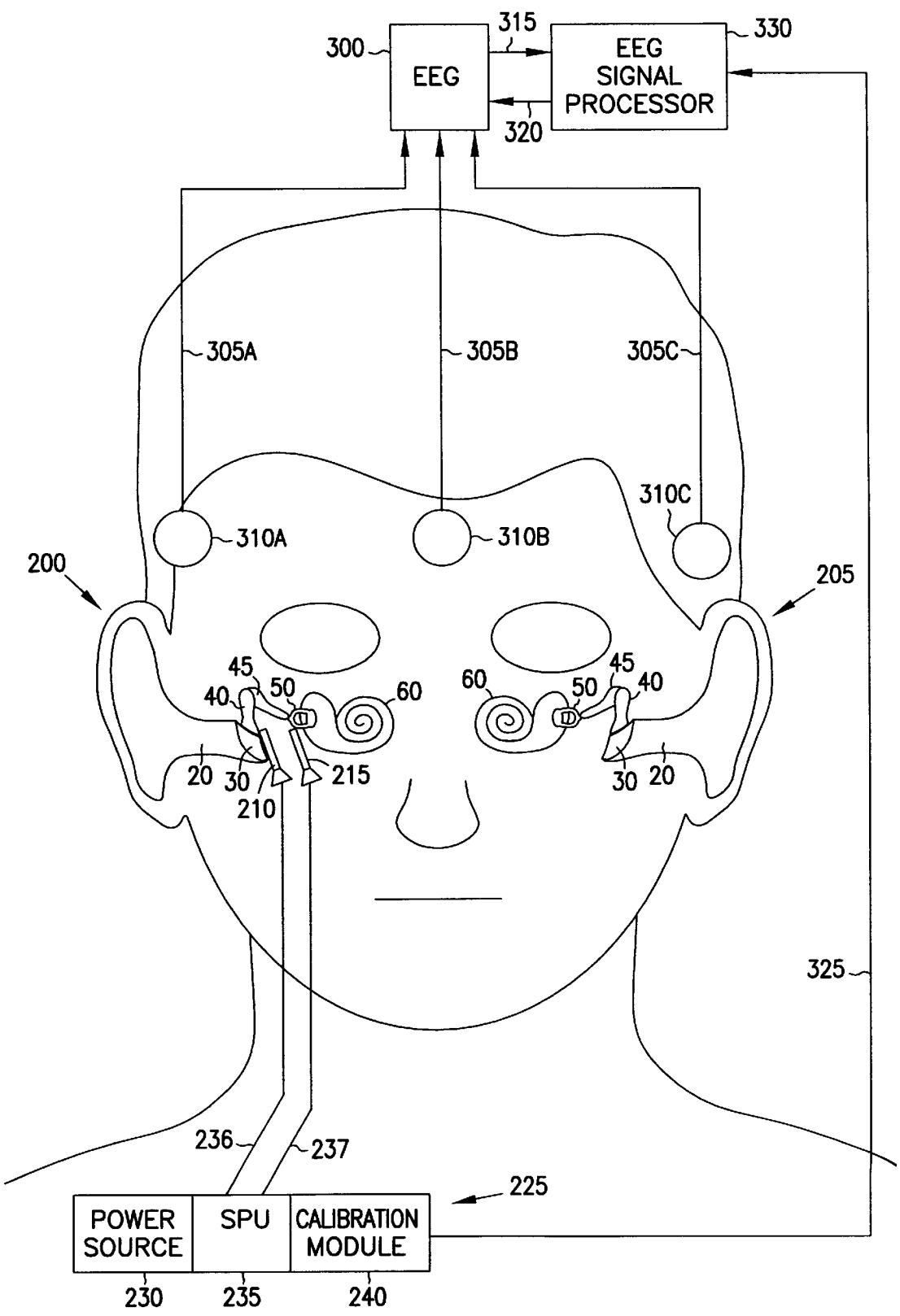
FIG. 3 further illustrates the embodiment of FIG. 2, including a triggering signal provided to an EEG signal processor.

FIG. 3 is a generalized schematic illustration of one embodiment of a synchronized mode of extracting the auditory response signal. In FIG. 3, calibration module 240 provides a trigger signal through signal path 325 to EEG signal processor 330. Signal path 325 may be an electrically coupled signal, a telemetered signal, or any other suitable means of communicating timing information about the calibration stimuli to EEG signal processor 330. In one embodiment, EEG signal processor 330 uses a measuring window, of similar duration as the time interval between calibration stimuli, to perform its averaging and correlation functions. An average auditory response signal is obtained by measuring the auditory response signals to multiple calibration stimuli. Alternatively, if electrical access to output lead 237 is available, the calibration output signal can be monitored on output lead 237 to provide timing information to EEG signal processor 330.

Calibration module 240 may be incorporated into SPU 235, either as hardware circuitry or as a set of instructions executed by a microprocessor therein. Calibration module 240 is typically capable of providing different calibration output signals to output stimulator 215 resulting in different calibration stimuli. For example, the calibration output signals and corresponding calibration stimuli may comprise a series of wide-band audio frequency clicks at a known, controllable repetition frequency. In another example, the wide-band audio click includes superimposed high-pass noise, i.e. noise above an adjustable cutoff frequency. Adjusting the cutoff frequency thereby varies the frequency content of the calibration stimuli, from which different average auditory response signals are obtained in response thereto. Yet another embodiment provides an audio frequency substantially pure tone burst. The frequency of the pure tone burst is adjusted between several discrete frequencies in the audio frequency range, such as at 500 Hz, 1 kHz, 2 kHz, 4 kHz and 8 kHz for obtaining corresponding average auditory response signals at each such discrete frequency.

The diagnostic and calibration capabilities of the present invention are particularly useful during surgical implantation of hearing assistance system components into a patient under general anesthesia. In particular, the present invention allows the physician to ascertain efficacy and adjust therapy accordingly.

For example, in implanting output stimulator 215 in the middle 35 or inner ear regions, the physician can place calibration module 240 in an unsynchronized mode delivering repeated constant amplitude calibration stimuli. EEG device 300 and EEG signal processor 330 provide the resulting average auditory response signal and other diagnostic information. The physician can position and affix output stimulator 215 in such a manner that maximizes the average auditory response signal that is obtained.

After the output stimulator has been positioned and affixed, the calibration stimuli are discontinued and audio frequency signals are applied, such as by an earphone placed in the external auditory canal 20. The physician can then position and affix input transducer 210 and adjust the signal processing parameters in SPU 235, such as amplification gain and filter rolloff frequencies, to obtain the desired auditory response signal.

The present invention also offers advantages subsequent to the positioning and affixing of input transducer 210 and output stimulator 215. Signal processing parameters in SPU 235 can be adjusted based upon the average auditory response signal and other diagnostic information provided by EEG device 300 and EEG signal processor 330 resulting from the output stimuli or calibration stimuli.

Figure 4:
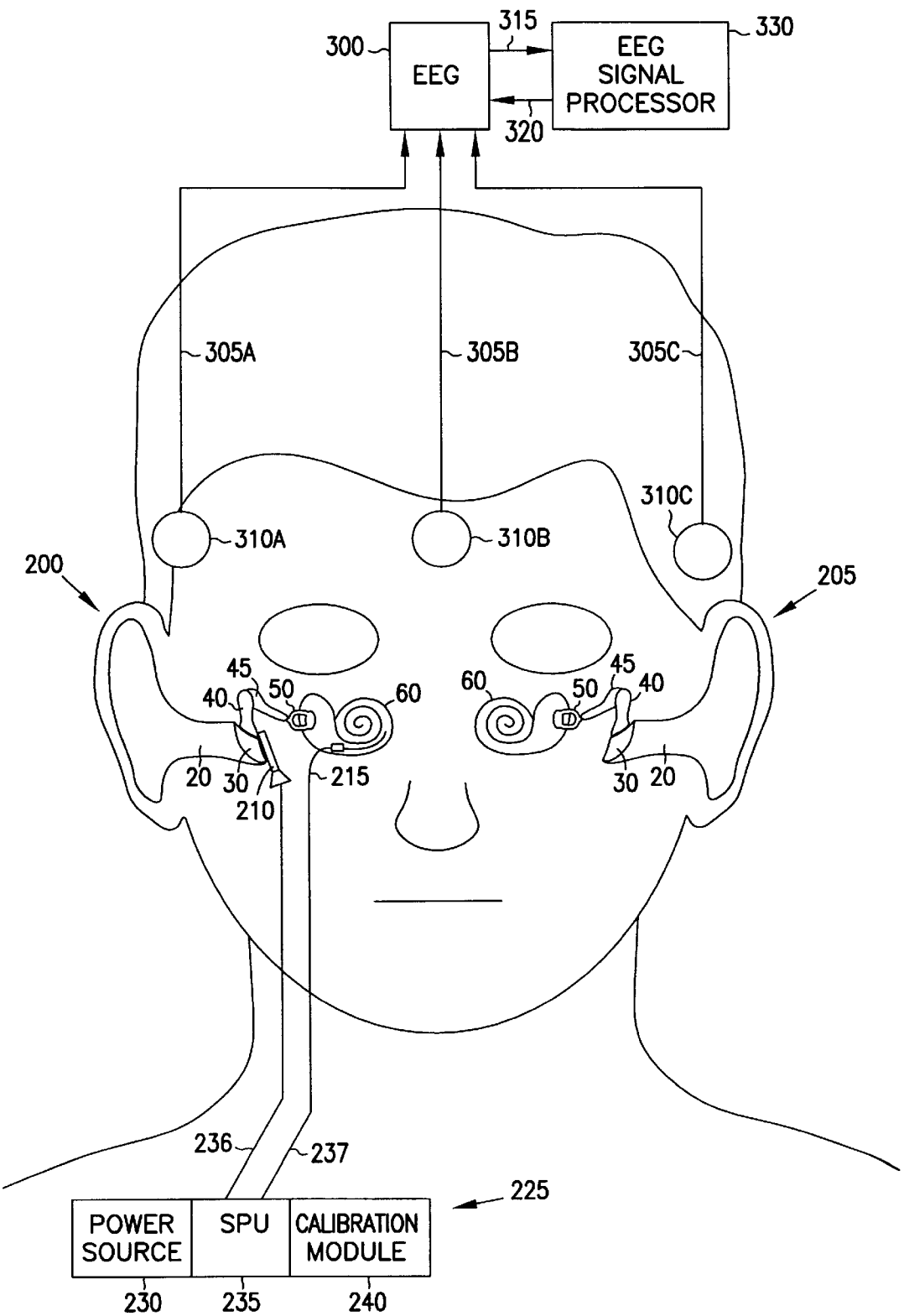
FIG. 4 is a generalized schematic illustration of a frontal view of a person with cutaway views of each ear, including an embodiment of the invention comprising a cochlear implant output stimulator.

FIG. 4 is a generalized schematic illustration of another embodiment of the invention including a frontal view of a person in which it is used. FIG. 4 includes some of the features of the invention described with respect to FIG. 2, but the output stimulator 215 comprises a single channel or multiple channel cochlear implant rather than an electromechanical output transducer. In this embodiment, the output stimuli are typically electrical stimuli rather than mechanical vibrations. The cochlear implant output stimulator 215 is typically disposed in cochlea 60 by insertion either through the oval window 55, round window 65, or elsewhere, or is disposed elsewhere in the inner ear region. In this embodiment, signal processing unit 235 includes cochlear implant processing capability, and output lead 237 includes an appropriate configuration of conductors corresponding to the particular type (i.e., single channel or multiple channel) of cochlear implant output stimulator 215.

Figure 5:
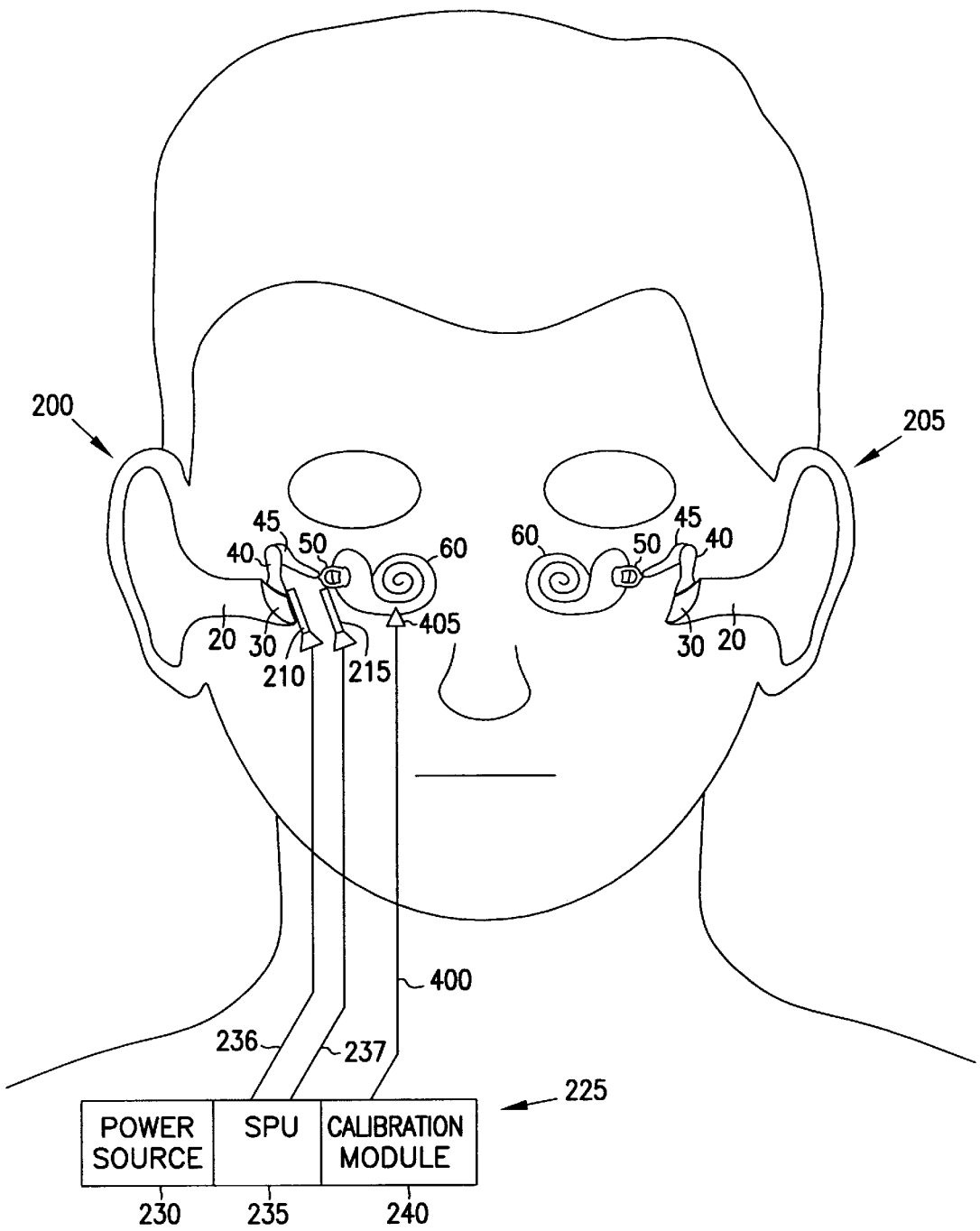
FIG. 5 is a generalized schematic illustration of a frontal view of a person with cutaway views of each ear, including an embodiment of the invention comprising an implanted sensor for receiving an electrical auditory response signal.

FIG. 5 is a generalized schematic illustration of another embodiment of the invention including a frontal view of the person in which it is used. Unlike the embodiment illustrated in FIG. 2, in the embodiment of FIG. 5 the auditory response signal to output or calibration stimuli is received by an implanted portion of the invention rather than by an external response sensor that includes surface electrodes 310A–C, external leads 305A–C, and external EEG device 300. In one such embodiment, electronics unit 225 receives an electrocochleographic or other auditory response signal through response lead 400 from implantable response sensor 405 or other mechanism for receiving a feedback signal such as the auditory response signal. The auditory response signal received through response lead 400 results either from calibration stimuli introduced into the middle ear 35 or inner ear regions, or from output stimuli provided in the middle ear 35 or inner ear in response to sound waves or mechanical vibrations received from input transducer 210 and processed by electronics unit 225.

In one embodiment, response sensor 405 includes at least one electrode placed on the bone of the promontory or in contact with cochlea 60 or the auditory nerve such that response sensor 405 is in close proximity with the cochlear sites that generate electric potentials in response to internal cochlear pressures resulting from sound. The technique of obtaining an auditory response signal from response sensor 405, which is located as described above, is referred to as electrocochleography. Electrocochleography typically provides a good prediction of the patient's audiometric threshold, but only measures the most peripheral portion of the patient's auditory system.

Figure 6:
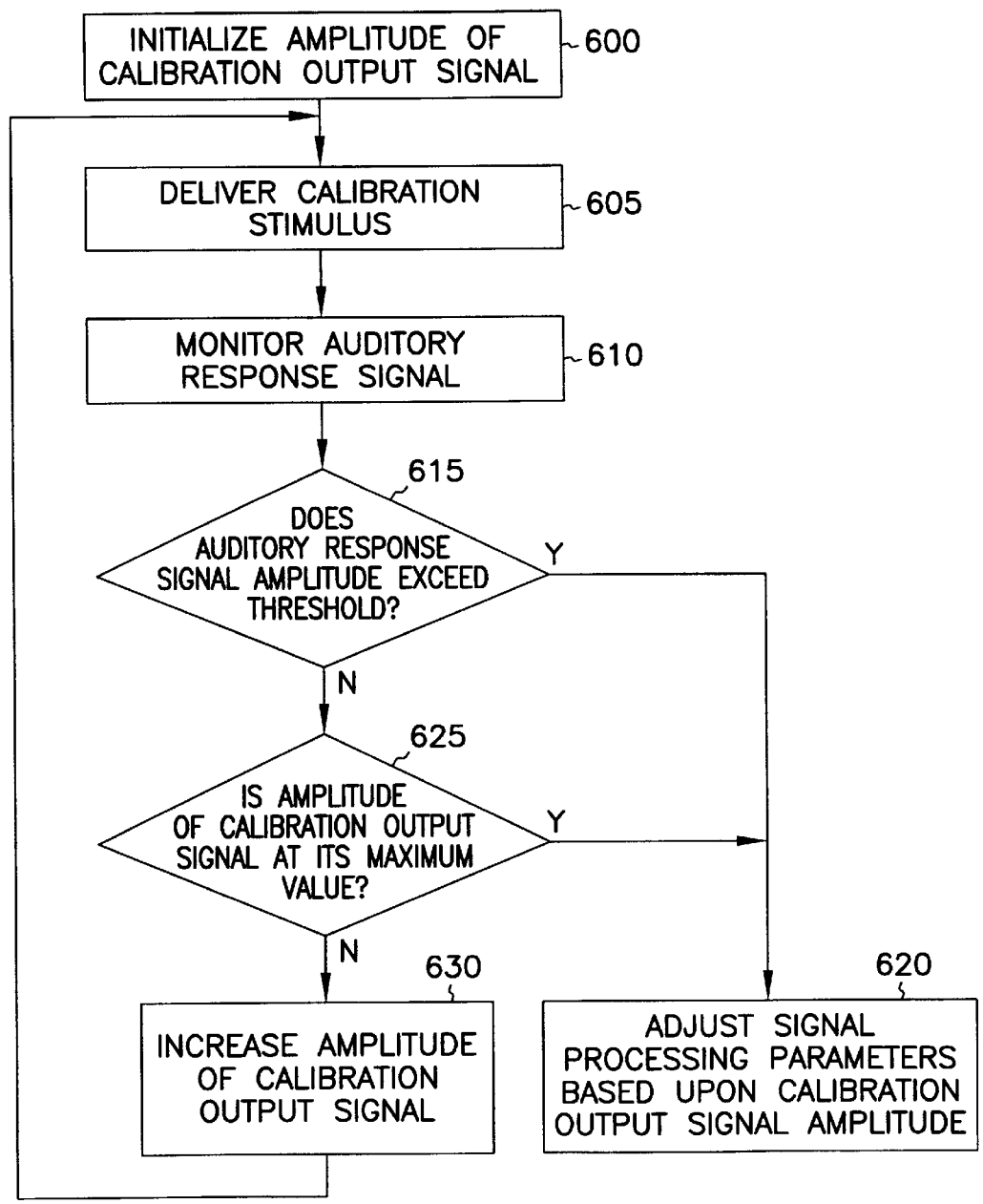
FIG. 6 is a flow chart illustrating one embodiment of a self-calibration function provided by the invention, such as by the embodiment of FIG. 5.

FIG. 6 is a flow chart illustrating one embodiment of a self-calibration function provided by the invention, such as by the embodiment of FIG. 5. At step 600, the amplitude of the calibration output signal is initialized to a value at the lower end of a range of possible amplitude values. At step 605, a calibration stimulus is delivered, such as by output stimulator 215, in response to the calibration output signal provided by electronics unit 225. At step 610, an auditory response signal is monitored. In one embodiment, the auditory response signal is provided by response sensor 405 in response to the calibration stimulus. At step 615, if the amplitude of the auditory response signal exceeds a programmably adjustable threshold value, at least one signal processing parameter, such as amplification gain in SPU 235, is adjusted accordingly at step 620. At step 615, if the amplitude of the auditory response signal does not exceed the programmably adjustable threshold value, and if the amplitude of the calibration output signal is not yet at its maximum value at step 625, the amplitude of the calibration output signal is increased at step 630. A calibration stimulus is then delivered at step 605 in response to the higher amplitude calibration output signal in order to further test for an adequate auditory response signal.

Figure 7:
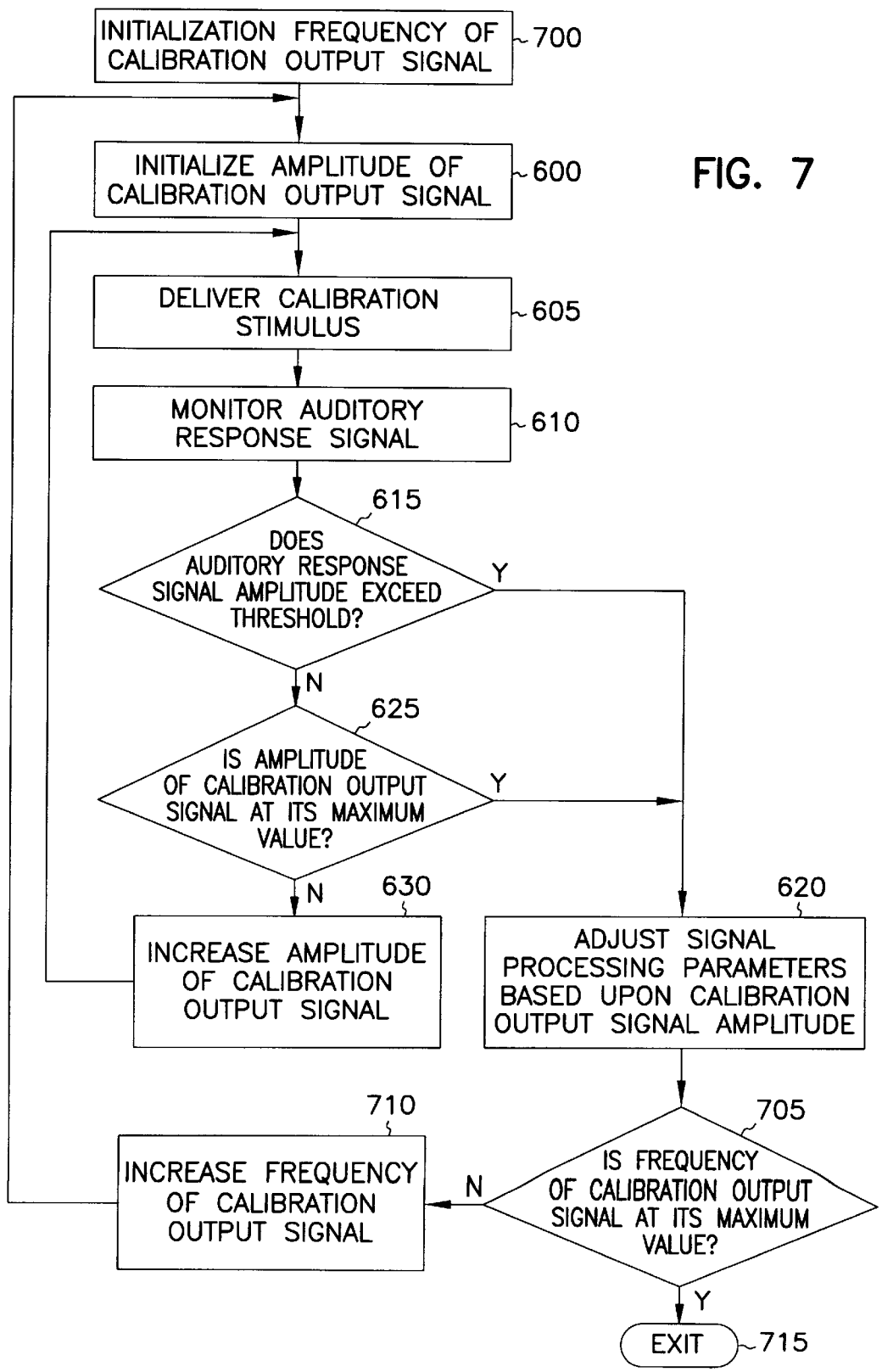
FIG. 7 is a flow chart illustrating another embodiment of a frequency-response self-calibration function provided by the invention, such as by the embodiment of FIG. 5.

FIG. 7 is a flow chart illustrating another embodiment of a frequency-response self-calibration function provided by the system. The frequency response self-calibration function is similar to the embodiment described with respect to FIG. 6, except that it is performed over a range of frequencies, such as over the audio range of frequencies. At step 700, the frequency of the calibration output signal is initialized to a frequency at or near one end of the audio range of frequencies, such as, for example, 500 Hz. The self-calibration is performed at that frequency according to the method described with respect to FIG. 6. At step 620, signal processing parameters are adjusted, such as based upon the calibration output signal amplitude for the particular frequency of calibration output signal. If, at step 705, the frequency of the calibration output signal has not yet reached a value at the opposite end of the audio frequency range, such as a maximum calibration output signal frequency of approximately 10 kilohertz, the frequency of the calibration output signal is incremented at step 710. The self-calibration is then repeated at step 600 using the new frequency of calibration output signal. When at step 705 the frequency of the calibration output signal has reached its maximum value, the self-calibration of FIG. 7 is exited at step 715. In this way, signal processing parameters are adjusted to obtain a self-calibrated frequency response.

Figure 8:
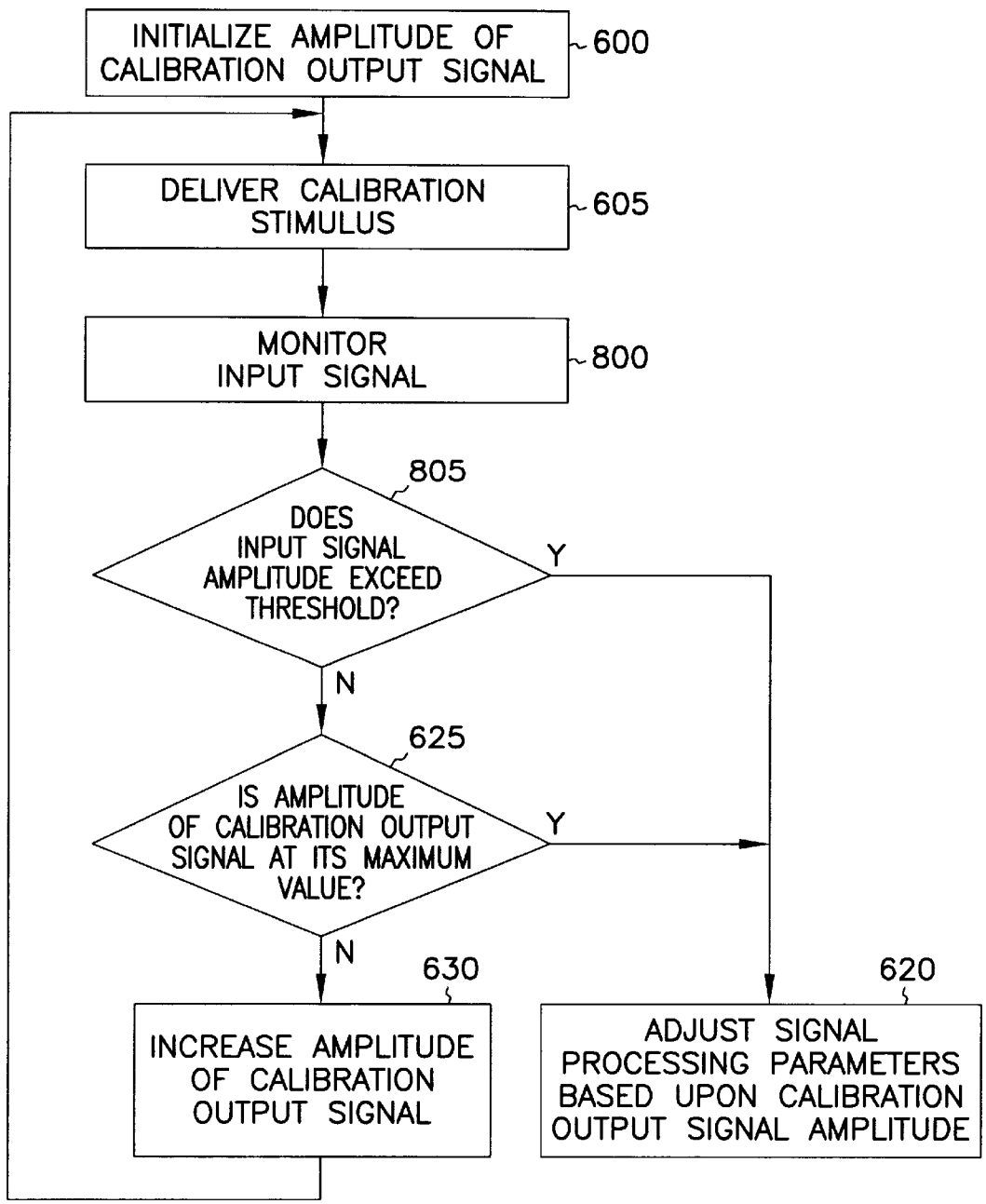
FIG. 8 is a flow chart illustrating one embodiment of a feedback self-test function provided by the invention, such as by the embodiment of FIG. 5.

FIG. 8 is a flow chart illustrating another embodiment of a feedback self-test function provided by the invention, such as by the embodiment of FIG. 5. It is possible for mechanical vibrations provided by output stimulator 215 to generate an undesirable mechanical positive feedback signal which vibrates input transducer 210. Such mechanical feedback can result from any mechanical or acoustic coupling in the middle ear. In particular, if incus 45 is not removed, it may provide a mechanical feedback path for vibrations from output stimulator 215 to input transducer 210. FIG. 8 illustrates one embodiment of a feedback-self test for detecting the presence of mechanical feedback, and adjusting signal processing parameters accordingly.

At step 600, the amplitude of the calibration output signal is initialized to a value at the lower end of a range of possible amplitude values. At step 605, a calibration stimulus is delivered, such as by output stimulator 215 in response to the calibration output signal provided by electronics unit 225. At step 800, an input signal is monitored, such as by input transducer 210 or other mechanism for detecting a feedback signal, for mechanical feedback resulting from the calibration stimulus provided by output stimulator 215. At step 805, if the amplitude of the input signal exceeds a programmably adjustable threshold value, signal processing parameters, such as amplification gain in SPU 235, are adjusted at step 620 to reduce the effect of the feedback. At step 805, if the amplitude of the input signal does not exceed the programmably adjustable threshold value, and if the amplitude of the calibration output signal is not at its maximum value at step 625, the amplitude of the calibration output signal is increased at step 630. A calibration stimulus is then delivered at step 605 in response to the higher amplitude calibration output signal to further test for the presence of mechanical feedback.

In another embodiment, the system of FIG. 5 provides a feedback signal or an automatic gain control (AGC) function using electrocochleography. Electronics unit 225 either periodically or continuously monitors the amplitude of the auditory response signal received through response lead 400 from response sensor 405. Electronics unit 225 adjusts signal processing parameters, such as amplification gain in SPU 235, based upon the amplitude of the received auditory response signal. In one embodiment, for example, the amplification gain is adjusted in SPU 235 such that the response signal obtained from response sensor 405 is maintained at an approximately constant amplitude.

Figure 9:
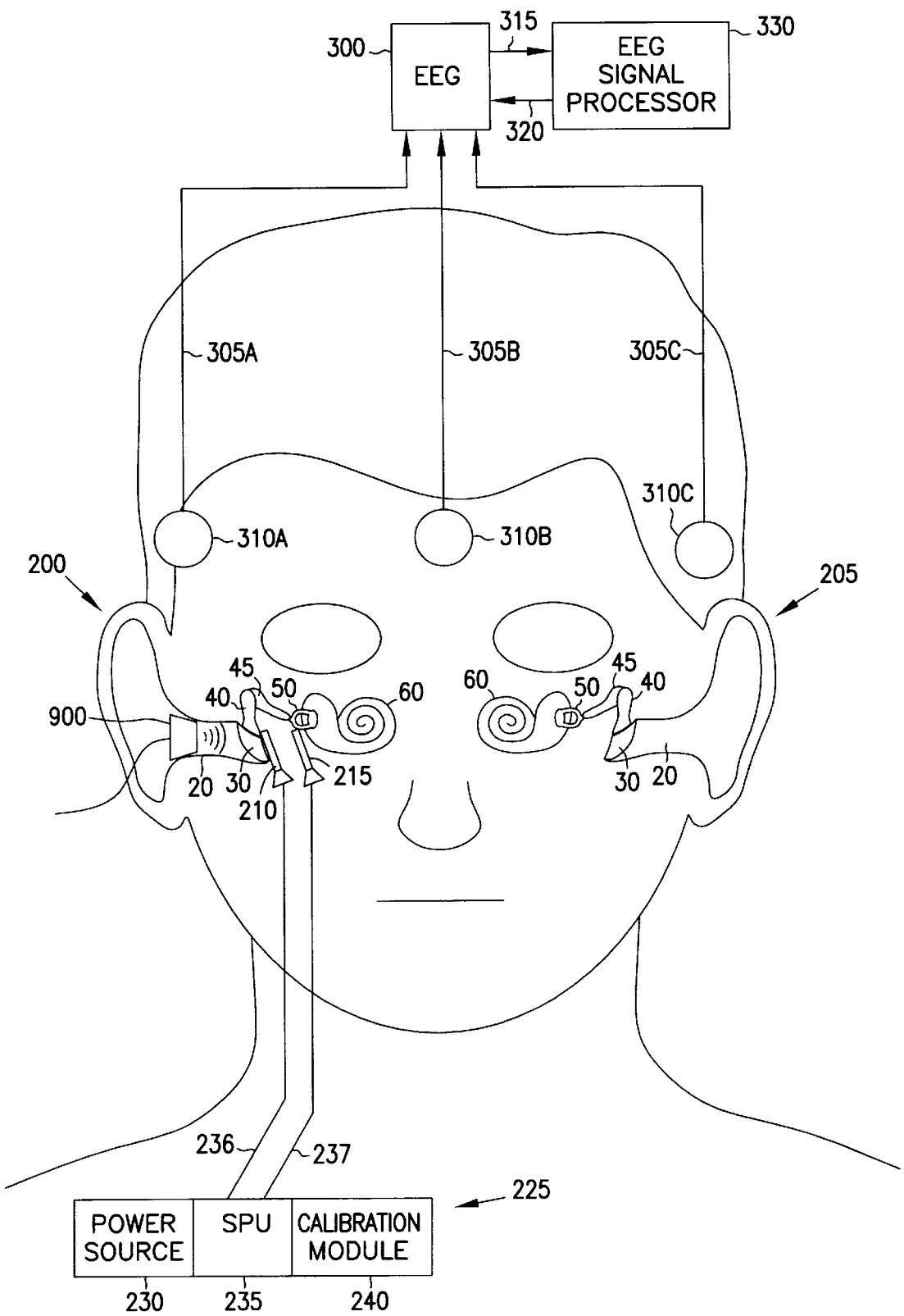
FIG. 9 is a generalized schematic illustration of a frontal view of a person with cutaway views of each ear, including an embodiment of the invention which receives sound externally and provides a resulting auditory response signal.

FIG. 9 is a generalized schematic illustration of another embodiment of the present invention. FIG. 9 illustrates that though the system has been described with particular emphasis on its calibration and diagnostic capabilities, it is intended to include any use of electrical response audiometry (EAR) techniques in conjunction with any at least partially implantable hearing assistance system. In FIG. 9, sounds are provided, such as through external earphone 900 placed in the external auditory canal 20. The sounds are converted to mechanical vibrations by tympanic membrane 30. Either the sounds or the associated mechanical vibrations are sensed by input transducer 210, which is disposed in the external auditory canal 20 or middle ear 35 region to produce a resulting electrical input signal. The resulting electrical input signal is provided through input lead 236 to electronics unit 225, and processed by electronics unit 225 to provide a resulting electrical output signal. The output signal is provided through output lead 237 to output stimulator 215 to provide an electrical or mechanical output stimulus to the middle ear 35 or inner ear regions. Brain waves are monitored and an auditory response signal is extracted from a response sensor, such as by EEG device 300 and EEG signal processor 330, or by an implanted response sensor 405 as illustrated in FIG. 5.

Thus, the present invention provides a hearing assistance system having built-in diagnostic and calibration capability that is particularly useful during the surgical implantation procedure, in order to ascertain efficacy and adjust therapy accordingly. The system also includes self-calibration, frequency-response self-calibration, feedback self-test, and automatic gain control (AGC) embodiments in order to increase its ease of use.

It is to be understood that the above description is intended to be illustrative, and not restrictive. Many other embodiments will be apparent to those of skill in the art upon reviewing the above description. For example, though the invention is described with respect to disposition of components within one ear, the invention is intended to include any embodiment in which components in either or both ears. More particularly, input transducer 210 could be disposed in right ear 200 and output stimulator 215 could be disposed in left ear 205, or vice-versa. In embodiments having an implanted response sensor 405, the response sensor 405 is typically disposed in the same ear as the output stimulator 215. The scope of the invention should, therefore, be determined with reference to the appended claims, along with the full scope of equivalents to which such claims are entitled.

What is claimed is:

1. A method of using an at least partially implantable hearing assistance device, the method comprising the steps of:

(a) providing a calibration stimulus to the middle or inner ear via an output stimulator, the output stimulator being proportioned for disposition within a middle ear region or an inner ear region;

(b) detecting a feedback signal; and (c) changing a characteristic of the calibration stimulus based upon the detected feedback signal.

2. The method of claim 1, wherein the step of changing a characteristic of the calibration stimulus comprises the step of adjusting the amplitude of the calibration stimulus if the detected feedback signal does not meet a threshold.

3. The method of claim 1, further comprising the step of:

(d) adjusting a signal processing parameter if the detected feedback signal meets a threshold.

4. The method of claim 3, wherein steps (a)–(d) are repeated using calibration stimuli of different frequencies.

5. The method of claim 1, wherein the feedback signal is detected at an input transducer.

6. The method of claim 1, wherein the feedback signal is detected at a response sensor.

7. An apparatus. comprising:

an input transducer for converting a sound vibration into an electrical input signal;

an output stimulator, proportioned for disposition within a middle ear region or an inner ear region and providing an output stimulus thereto in response to an electrical output signal;

an electronics unit that receives the input signal and provides the output signal to the output stimulator; and a calibration module, which is carried by the electronics unit, for providing a calibration output signal to the output stimulator;

wherein the output stimulator provides a calibration stimulus in response to the calibration output signal received from the electronics unit.

8. The apparatus of claim 7, wherein the input transducer provides a feedback signal, resulting from the calibration stimulus, to the electronics unit.

9. The apparatus of claim 8, wherein a signal processing parameter is adjusted based upon the feedback signal.

10. The apparatus of claim 7, further comprising a response sensor for measuring an auditory response signal resulting from the calibration stimulus.

11. The apparatus of claim 10, wherein the response sensor is electrically coupled to the electronics unit for providing the auditory response signal thereto.

12. The apparatus of claim 11, further comprising a calibration module that adjusts characteristics of the calibration output signal based upon the auditory response signal.

13. The apparatus of claim 11, wherein the electronic unit comprises a signal processing unit, said signal processing unit comprising signal processing means to adjust a signal processing parameter according to a self-calibration function based upon the auditory response signal.

14. The apparatus of claim 7, wherein the electronics unit is configured to be implanted in the mastoid portion of a patient's temporal bone.

15. The apparatus of claim 7, wherein the electronics unit is configured to be implanted in a patient's pectoral region.

* * * * *